(12) United States Patent
Shah (10) Patent No.: US 7,762,982 B1
(45) Date of Patent: Jul. 27, 2010

(54) BREAST IMPLANT FILL DEVICE

(76) Inventor: Darshan Shah, P.O. Box 11630, Bakersfield, CA (US) 93389

(*) Notice: Subject to any disclaimer, the term of this patent is extended or adjusted under 35 U.S.C. 154(b) by 1611 days.

(21) Appl. No.: 11/023,245

(22) Filed: Dec. 27, 2004

(51) Int. Cl.
*A61M 29/00* (2006.01)
*A61M 31/00* (2006.01)
*A61F 2/52* (2006.01)
*A61F 2/12* (2006.01)

(52) U.S. Cl. .............. 604/96.01; 623/7; 623/8; 604/65

(58) Field of Classification Search .............. 604/96.01, 604/65–67, 131; 623/7, 8
See application file for complete search history.

(56) References Cited

U.S. PATENT DOCUMENTS

| | | | |
|---|---|---|---|
| 2,766,907 A | 10/1956 | Wallace, Jr. | |
| 4,090,514 A | 5/1978 | Hinck et al. | |
| 4,507,116 A | 3/1985 | Leibinsohn | |
| 4,624,671 A | 11/1986 | Kress | |
| 4,735,613 A | 4/1988 | Bellin et al. | |
| 4,955,905 A | 9/1990 | Reed | |
| 5,531,679 A * | 7/1996 | Schulman et al. | 604/65 |
| 5,549,672 A | 8/1996 | Maddock et al. | |
| 5,744,027 A * | 4/1998 | Connell et al. | 210/96.2 |
| 5,954,696 A | 9/1999 | Ryan | |
| 6,432,081 B1 | 8/2002 | Atala | |
| 6,944,638 B1 * | 9/2005 | Putnam | 708/206 |
| 2003/0074084 A1 | 4/2003 | Nakao | |
| 2004/0260232 A1 * | 12/2004 | Cimino | 604/65 |

FOREIGN PATENT DOCUMENTS

| | | |
|---|---|---|
| GB | 2042091 | 9/1980 |
| WO | WO99/15756 | 4/1999 |

* cited by examiner

*Primary Examiner*—Kevin C Sirmons
*Assistant Examiner*—Michael J Anderson
(74) *Attorney, Agent, or Firm*—Michael I Kroll (57) ABSTRACT

A system for pumping a fluid into an object for insertion into the human body comprising a housing having a pump chamber with means for pumping said fluid therein. A source of fluid is connected to the pumping means and a value is connected to the pumping mechanism and the object. The housing includes means connected to the pumping means for entering an amount of the fluid to be pumped thereby. Upon entering a desired amount of fluid in the entering means, the pumping means causes an amount of the fluid equal to the entered amount to be pumped through the pump chamber and further through the valve to fill the object with the desired amount of fluid.

7 Claims, 7 Drawing Sheets

BREAST IMPLANT FILL DEVICE

BACKGROUND OF THE INVENTION

1. Field of the Invention

The present invention relates generally to pressure infusion devices and, more specifically, to an electronic breast implant device that is programmable to deliver a precise amount of fluid to an implant during surgery. The pump includes a pump device that will draw saline through a tube from a saline bag and pump the saline into an implant. The pump device will maintain a closed system that will prevent air and infectious contaminants from being introduced to the fluid. The pump device is reversible thereby enabling the surgeon to remove fluid as needed. A digital keyboard and display allow the surgeon to preset the desired amount of saline to be distributed to the implant and let the surgeon concentrate on the surgery while the implant is being filled. A three-way valve is disposed in the line between the pump device and the implant to enable the surgeon to insert a syringe therein to manually make fine adjustments to the quantity of fluid in the implant.

2. Description of the Prior Art

Surgeons performing breast augmentation surgery using saline implants presently use a manual hand pump to deliver saline to the implants which is time consuming and requires the surgeon to concentrate on keeping count of how many cc's of fluid have been transferred. Unfortunately, there are frequent distractions in the operating room that require the surgeons attention simultaneously that could result in the surgeon losing count and delivering the improper amount of saline. Furthermore, the additional amount of time spent in the operating room adds to the cost to the patient and reduces the amount of time that the surgeon and staff can be performing other duties and that the operating room may be used for other patients.

The present invention seeks to overcome the shortcomings of the prior art by introducing a breast implant fill pump device utilizing a peristaltic pump, cardiac pump or any other suitable pump device that will draw saline through a tube from a saline bag and pump the saline into an implant. The pump device will maintain a closed system that will prevent air and infectious contaminants from being introduced to the fluid. The pump device is reversible thereby enabling the surgeon to remove fluid as needed. A digital keyboard and display allow the surgeon to preset the desired amount of saline to be distributed to the implant and let the surgeon concentrate on the surgery while the implant is being filled.

There are other pressure infusion devices designed for delivering fluid. Typical of these is U.S. Pat. No. 2,766,907 issued to Wallace, Jr. on Oct. 16, 1956.

Another was issued to Hinck et al. on May 23, 1978 as U.S. Pat. No. 4,090,514. Yet another U.S. Pat. No. 4,507,116 was issued to Leibinsohn on Mar. 26, 1985 and still yet another was issued on Nov. 25, 1986 to Kress as U.S. Pat. No. 4,625,671.

Another was issued to Bellin et al. on Apr. 5, 1988 as U.S. Pat. No. 4,735,613. Yet another U.S. Pat. No. 4,955,905 was issued to Reed on Sep. 11, 1990 and still yet another was issued on Aug. 27, 1996 to Maddock et al. as U.S. Pat. No. 5,549,672.

Another was issued to Ryan on Sep. 21, 1999 as U.S. Pat. No. 5,954,696. Yet another U.S. Pat. No. 6,432,081 was issued to Atala on Aug. 13, 2002 and still yet another was published on Apr. 17, 2003 to Nakao as U.S. Patent Publication No. 2003/0074084.

Another patent was issued to Godrich et al. on Sep. 17, 1980 as U.K. Patent No. GB2 042 091 and another was published on Apr. 1, 1999 as International Patent Application No. WO99/15756 to Corlew.

U.S. Pat. No. 2,766,907

Inventor: James M. Wallace, Jr.

Issued: Oct. 16, 1956

Apparatus for pressure infusion of liquids comprising an open-ended container having walls of flexible, substantially inextensible material adapted to contain an inner flexible, collapsible receptacle filled with liquid to be infused, an expansible bladder disposed within said container adjacent one wall thereof adapted to be inflated to press against said receptacle in said container to force liquid therefrom, means for releasable securing said bladder in place within said container, and means comprising a cinching strap for restricting said container adjacent its open end for releasably retaining said receptacle in place in said container.

U.S. Pat. No. 4,090,514

Inventor: Howard Helmut Hinck et al.

Issued: May 23, 1978

A pressure infusion device includes a bladder as part of the cuff in which a fluid filled plastic bag is encased wherein the bladder surrounds at least eighty percent of the plastic bag, and, upon fluid being pumped into the bladder, the fluid in the plastic bag is infused under pressure to a patient.

U.S. Pat. No. 4,507,116

Inventor: Saul Leibinsohn

Issued: Mar. 26, 1985

Apparatus for the induced infusion of a liquid from a flexible liquid bag comprises a pumping bulb, elastic inflatable means coupled to the bulb for inflation thereby, and a flexible sleeve for retaining the liquid bag firmly against a first portion of the inflatable means for applying the pressure thereof to the bag to induce infusion of the liquid therefrom. The elastic inflatable means includes a second portion which serves as an accumulator for accumulating pressurized fluid pumped by the bulb and comprises an outer non-elastic sheath for limiting the accumulation of the pressurized fluid therein. In one described embodiment, the two mentioned portions of the elastic inflatable means are constituted of separate units, one being a bag-presser including an inflatable bladder against which the liquid bag is pressed by the flexible sleeve, and the other being a separate accumulator including an inflatable tube enclosed by the non-elastic sheath. In a second described embodiment, both of the mentioned portions of the elastic inflatable means are constituted of a single elastic bladder enclosed only at its mid-portion by the flexible sleeve, the end portions of the bladder projecting outwardly of the flexible sleeve and being enclosed by the non-elastic sheath so as to serve as the accumulators for accumulating the pressurized fluid.

U.S. Pat. No. 4,624,671

Inventor: Donald W. Kress

Issued: Nov. 25, 1986

A method of sizing a breast prosthesis and implanting an accurately sized breast prosthesis is disclosed. The method involves implanting an empty, inflatable elastomeric balloon in a breast, filling the balloon with a liquid to a desired size, measuring the amount of liquid in the filled balloon, removing the liquid from the balloon, and removing the empty balloon from the breast. A final breast prosthesis is sized in accordance with the amount of liquid that was in the filled balloon. The properly sized final breast prosthesis is then implanted into the breast.

U.S. Pat. No. 4,735,613

Inventor: Matthew E. Bellin et al.

Issued: Apr. 5, 1988

A pressure infusion device for medical applications for applying pressure to a sealed bag of liquid, such as an I.V. bag, in which the pressure gauge is fastened directly in the pressure applying bag which presses against the I.V. bag. The gauge has a movable plunger which moves outwardly from the bag by an amount depending upon the pressure within the bag. The pressure infusion arrangement is designed to be relatively inexpensive so that it can be discarded after being used. There are two forms, one in which the I.V. bag is held against the pressure applying bag by a mesh which is secured to a fabric to form a pocket for the I.V. bag and the pressure applying bag. In the other form, the mesh is secured directly to the edge of the pressure applying bag.

U.S. Pat. No. 4,955,905

Inventor: Andrew M. Reed

Issued: Sep. 11, 1990

A pressure monitor for use in connection with tissue expander envelopes implanted beneath the tissue of the skin wherein a liquid is injected into the envelope to cause expansion of the skin or tissue and additional liquid is periodically injected to cause progressively increased expansion of the tissue. The tissue monitor includes means establishing direct communication between the pressure monitor and the liquid injected under pressure whereby the monitor will provide a reading of the internal liquid pressure in the envelope. The method comprises the steps of implanting an inflatable envelope beneath the skin, injecting a sterile solution under pressure through a fill line communicating with the envelope, interrupting the flow of liquid under pressure into the envelope, sensing the pressure level of liquid injected into the envelope, and adjusting the pressure level when necessary either by removing from or injecting liquid into the envelope.

U.S. Pat. No. 5,549,672

Inventor: Julie Maddock et al.

Issued: Aug. 27, 1996

Method and apparatus for filling mammary prostheses and tissue expanders using pumping systems are disclosed. In accordance with the method, a pumping system is used to deliver flow at the desired flow rate or pressure through a tube to the injection needle, allowing the surgeon to concentrate his attention on the injection itself to fill the inflatable mammary prosthesis or the tissue expander without having to operate and count filling syringes, all in a much faster manner than in the prior art. The pumping system used may include fluid volume measuring capabilities, pressure measuring capabilities, and other capabilities such as the capability, for viscosity reduction purposes, of heating the fluid to a temperature still compatible with injection. By providing the fluid in an appropriate bag with flexible tubing attached thereto, all in a sterile condition, the injection system and method of the invention provides a substantially closed system allowing fast and accurate filling of a mammary prosthesis or tissue expander with minimal opportunity for infection. Alternate methods and apparatus are disclosed.

U.S. Pat. No. 5,954,696

Inventor: Timothy C. Ryan

Issued: Sep. 21, 1999

A portable, ambulatory infusion pump for use with standard pre-filled infusion medicament containers is powered by a miniature compressed gas cylinder coupled to a mechanical pressure regulator which supplies regulated gas at a substantially constant pressure to an inflatable bladder. The bladder is positioned between a substantially rigid pressure surface and a moveable pressure transfer plate and pushes against the transfer plate when inflated. A pre-filled medicament container is positioned over the pressure transfer plate and is squeezed between the transfer plate and the pump housing cover as the plate is displaced in response to inflation of the flexible bladder. A safety interlock assembly is connected between the pressure regulator and the inflatable bladder and prevents inflation of the bladder unless the housing cover is completely closed. Upon inadvertent opening of the pump, the internal pressurization system is vented to atmosphere.

U.S. Pat. No. 6,432,081

Inventor: Anthony Atala

Issued: Aug. 13, 2002

Apparatus for the treatment of volume deficiency disorders of body structures and related syndromes and, more particularly, apparatus that delivers fluid via a catheter at a controlled pressure into a balloon situated within or adjacent to a body cavity to effect tissue expansion. A drainage mechanism, especially useful in treating bladder deficiencies, is disclosed which permits drainage of body fluids while the balloon is in its expanded state. The balloon can be adapted to fit within a recess of the catheter, for example, in a folded or rolled state, and the invention also provides means for delivering fluid at a controlled pressure into an inflatable balloon.

U.S. Patent Publication Number 2003/0074084

Inventor: Naomi Nakao

Published: Apr. 17, 2003

A method of breasts reconstruction utilizes a breast prosthesis having a plurality of chambers or compartments distributed through a body member or shell in the form of a breast. The chambers are disposed along the superior, lateral and inferior surfaces, as well as in the interior, of the body member. The chambers are differentially pressurized or filled in order to control the shape of the prosthesis upon implantation thereof. Valves are provided for regulating the flow of fluid into and from the chambers. The prosthesis and the fill levels of the respective chambers may be selected by computer.

U.K. Patent Number GB 2 042 091

Inventor: John Godrich et al.

Issued: Sep. 17, 1980

A drip feed arrangement, for feeding e.g. saline solution to a patient, has pressure means to apply a pressure, other than or in addition to that applied gravitationally, to urge the fluid through the drip tube. The pressure means can comprise means for applying pressure to the flexible bag 12 containing the saline solution, or a peristaltic pump acting on the feed tube 34. Power for the pressure means may be produced by the pump 19 driven by the chest expansion of the patient.

International Patent Publication Number
WO99/15756

Inventor: Edward A. Corlew

Published: Apr. 1, 1999

The invention discloses a system for controlling one or more borehole pumps to enable pumping-on-demand. The system uses a computerized controller which, in combination with sensors, monitors and controls the activity of the pump, thereby controlling fluid in the borehole. The system is continually in one of three modes, the monitoring mode, the pump mode, or the recovery mode. Within each cycle of modes, the system performs multiple checks on the apparatus involved. The data obtained during the check is stored in appropriate databases as well as checked against predetermined norms. In the event of a malfunction within the apparatus, or other supervised and/or monitored functions, the system can activate a notification system, such as a centralized monitoring facility. A pump is disclosed with a fluid sensor to detect the presence of fluid and transmit this presence to the computerized monitoring system. A slug sensor notifies the computer of the beginning and end of a predetermined quantity of fluid. An exterior housing with a lightning protector can be placed over the borehole to contain the monitoring computer and associated read outs. At least one shunt valve is affixed along the propellant and return lines inline to accommodate accumulation of fluid. A receiver/separator tank has a separator member to separate the gas from the fluid.

While these pressure infusion devices may be suitable for the purposes for which they were designed, they would not be as suitable for the purposes of the present invention, as hereinafter described.

SUMMARY OF THE PRESENT INVENTION

The present invention relates generally to pressure infusion devices and, more specifically, to an electronic breast implant device that is programmable to deliver a precise amount of fluid to an implant during surgery. The pump includes a pump device that will draw saline through a tube from a saline bag and pump the saline into an implant. The pump device will maintain a closed system that will prevent air and infectious contaminants from being introduced to the fluid. The pump device is reversible thereby enabling the surgeon to remove fluid as needed. A digital keyboard and display allow the surgeon to preset the desired amount of saline to be distributed to the implant and let the surgeon concentrate on the surgery while the implant is being filled. A three-way valve is disposed in the line between the pump device and the implant to enable the surgeon to insert a syringe therein to manually make fine adjustments to the quantity of fluid in the implant.

A primary object of the present invention is to provide an electronic breast implant fill device that overcomes the shortcomings of the prior art.

Another object of the present invention is to provide an electronic breast implant fill device for delivering a pre-determined amount of saline to the implant during breast augmentation surgery.

Another object of the present invention is to provide an electronic breast implant fill device that will negate the need for the surgeon to manually pump saline into the implant thereby saving time in the operating room, allowing the surgeon to concentrate on other tasks and reduce the risk of carpal tunnel syndrome that could result from constantly pumping the saline during each such surgery.

Still another object of the present invention is to provide an electronic breast implant fill device that monitors precisely how much fluid is in each implant.

Yet another object of the present invention is to provide an electronic breast implant fill device that eliminates the risk of air being pumped into the implant.

Still yet another object of the present invention is to provide an electronic breast implant fill device having a pump that is capable of transferring 1 liter of fluid through an IV tubing in under a minute thereby effectively reducing the amount of time required to fill each implant during surgery.

Yet another object of the present invention is to provide an electronic breast implant fill device that is simple and easy to use.

Still yet another object of the present invention is to provide an electronic breast implant fill device that is inexpensive to manufacture and operate.

Additional objects of the present invention will appear as the description proceeds.

The foregoing and other objects and advantages will appear from the description to follow. In the description reference is made to the accompanying drawings, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which.

DESCRIPTION OF THE REFERENCED NUMERALS

Turning now descriptively to the drawings, in which similar reference characters denote similar elements throughout the several views, the Figures illustrate the implant fill pump system of the present invention. With regard to the reference numerals used, the following numbering is used throughout the various drawing figures.

10 implant fill pump system
12 breast
14 power source
16 source
18 syringe
20 three-way valve
22 display
24 tube
26 fluid pump chamber
28 control pad
30 first implant
31 second implant
32 fluid
34 number of cc's pumped
36 program CC volume of fluids to be pumped
38 fluid vent
40 tubing retainer
41 center member
42 pumping mechanism
43 roller
44 housing
45 pumping direction
46 first implant button
48 second implant button
50 on/off switch
52 control pad numbers
54 delete-button
56 up-button
58 down-button
60 first implant tube
62 second implant tube
64 monitoring mechanism
66 audio alert
68 reverse pump button

DETAILED DESCRIPTION OF THE PREFERRED EMBODIMENT

The following discussion describes in detail one embodiment of the invention (and several variations of that embodiment). This discussion should not be construed, however, as limiting the invention to those particular embodiments. Practitioners skilled in the art will recognize numerous other embodiments as well. For definition of the complete scope of the invention, the reader is directed to appended claims.

Turning now descriptively to the drawings, in which similar reference characters denote similar elements throughout the several views, FIGS. 1 through 7 illustrate the implant fill pump system of the present invention which is indicated generally by the numeral 10.

Figure 1:
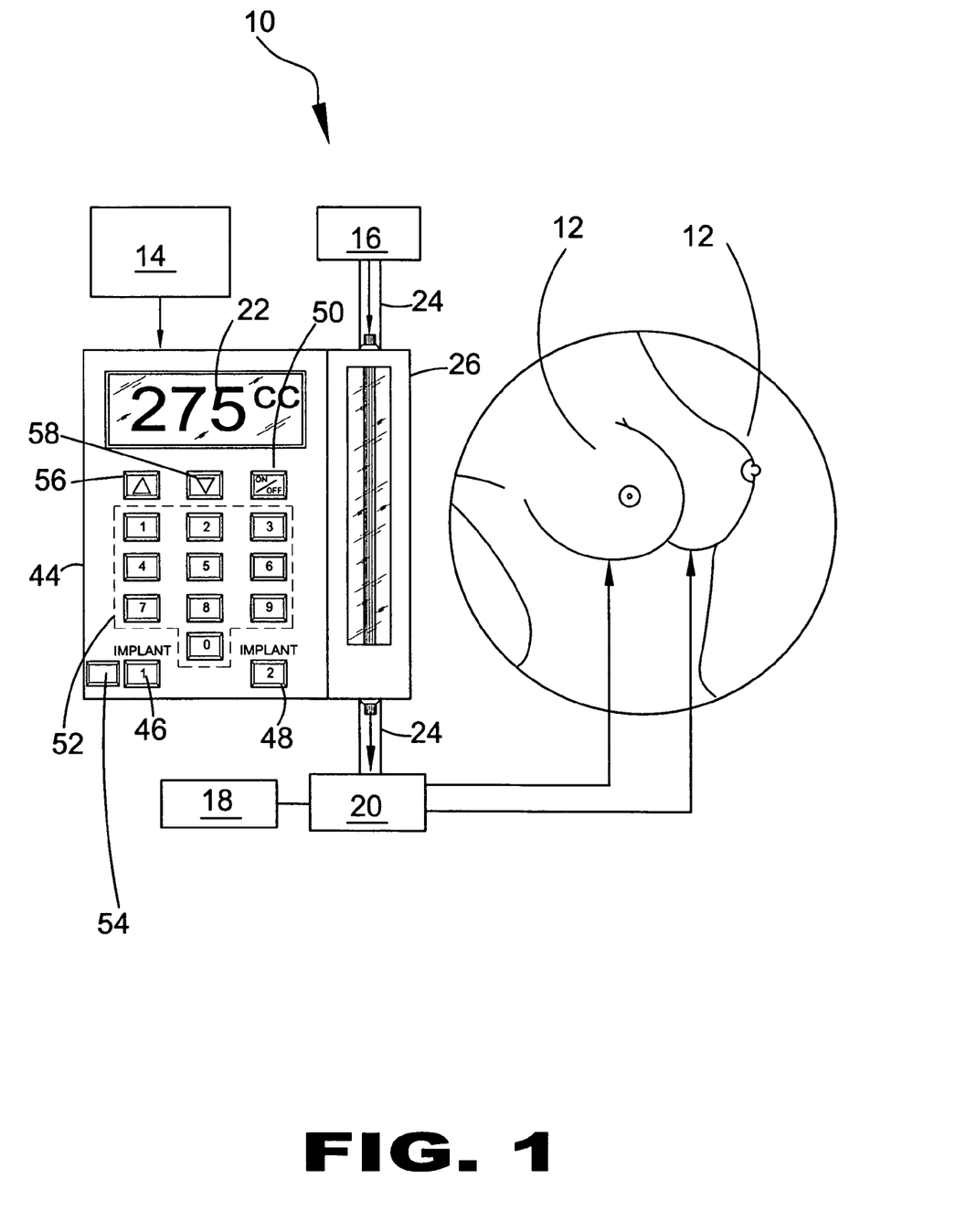
FIG. 1 is an illustrative view of the implant fill device of the present invention in use.

FIG. 1 is an illustrative view of the implant fill pump system 10 of the present invention. The implant fill pump system 10 is a programmable pump for breast implant fill having means for specifying an amount of material to be dispensed, and an auxiliary means forming an integral part therewith for varying the quantity of material dispensed.

The implant fill pump system 10 of the present invention comprises a power source 14, a housing 44, and a three-way valve 20. The power source 14 is attached to the housing 44 and supplies the power to the implant fill pump system 10. Housing 44 includes a control pad 28, a set digital readout display 22, and a display 23 positioned on a side thereof. The housing 14 also includes a translucent intravenous (IV) fluid pump chamber 26 for retaining a fluid therein. A fluid source 16 is attached to housing 44 via a tube 24. A portion of the tube 24 is placed in the fluid pump chamber 26. The remainder of the tube 24 extends externally from the housing 44 and is connected to a three-way valve 20. An first implant tube 60 extends from the three-way valve 20 to an a first implant 30, which is located in one of two breasts 12. A second implant tube 62 extends from the three-way valve 20 to a second implant 31, which is located in one of two breasts 12 that does not contain the first implant 30.

The system 10 of the present invention allows for the implants 30,31 to be precisely filled in cubic centimeter (cc) volume of fluid. The user programs the desired CC's of fluid using the control pad 28 to be pumped by the system to fill at least one of the first implant 30 and second implant 31. The user selectively depresses the at least one of the first implant button 46 and the second implant button 48, to fill the appropriate implant.

The implant fill pump system 10 pumps the user-specified amount of an fluid 32 from the source 16 through the tube 24, which travels through the fluid pump chamber 26 and connects to a first port of the three-way valve 20 positioned external to housing 44. As the fluid 32 is pumped through the three-way valve 20, a monitoring mechanism 64 senses the amount of fluid 32 that has passed therethrough. The amount of fluid sensed is then displayed on the display 22. To add fluid 32 to an implant 30,31, a user increases the amount using the keypad 28 and the newly increased amount is shown on the display 22.

Figure 7:
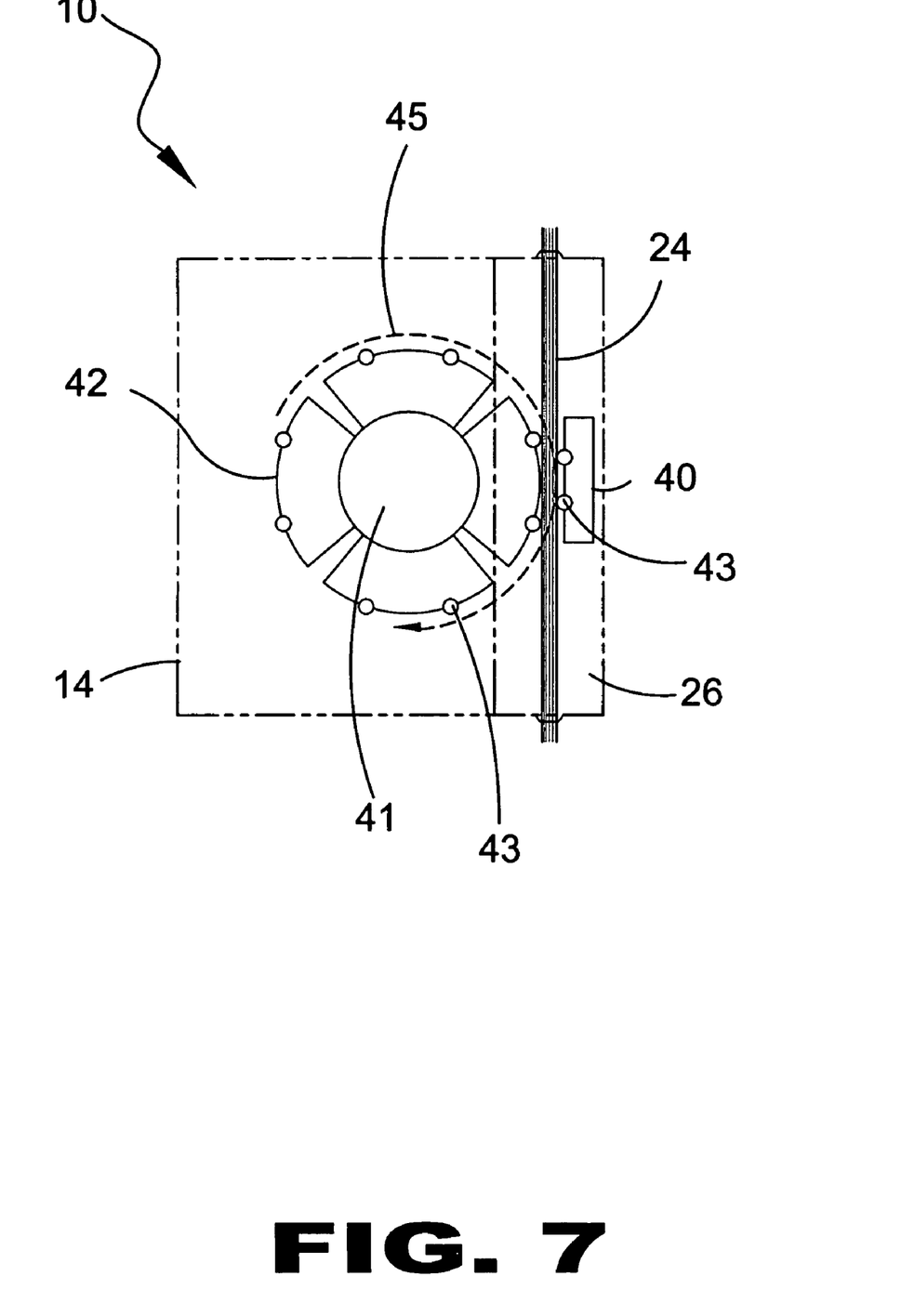
FIG. 7 is an illustrative view of the pump of the implant fill device of the present invention.

The fluid pump chamber 26 contains a pumping mechanism 42 as shown in FIG. 7, including but not limited to a peristaltic or a cardiac pump, which pumps the user-specified amount of fluid 32 in the tube 24 through the three-way valve 20 and into one of first implant tube 60 and further to the first implant 30 or the second implant tube 62 and further to the second implant 31.

To manually make fine adjustments to the quantity of fluid 32 contained in either the first implant 30 or second implant 31, the three-way valve 20 permits the user to attach a syringe 18 a port of three-way valve 20. Upon connecting the syringe 18, the physician is able to move the plunger to finely adjust the amount of fluid 32 contained therein.

Figure 2:
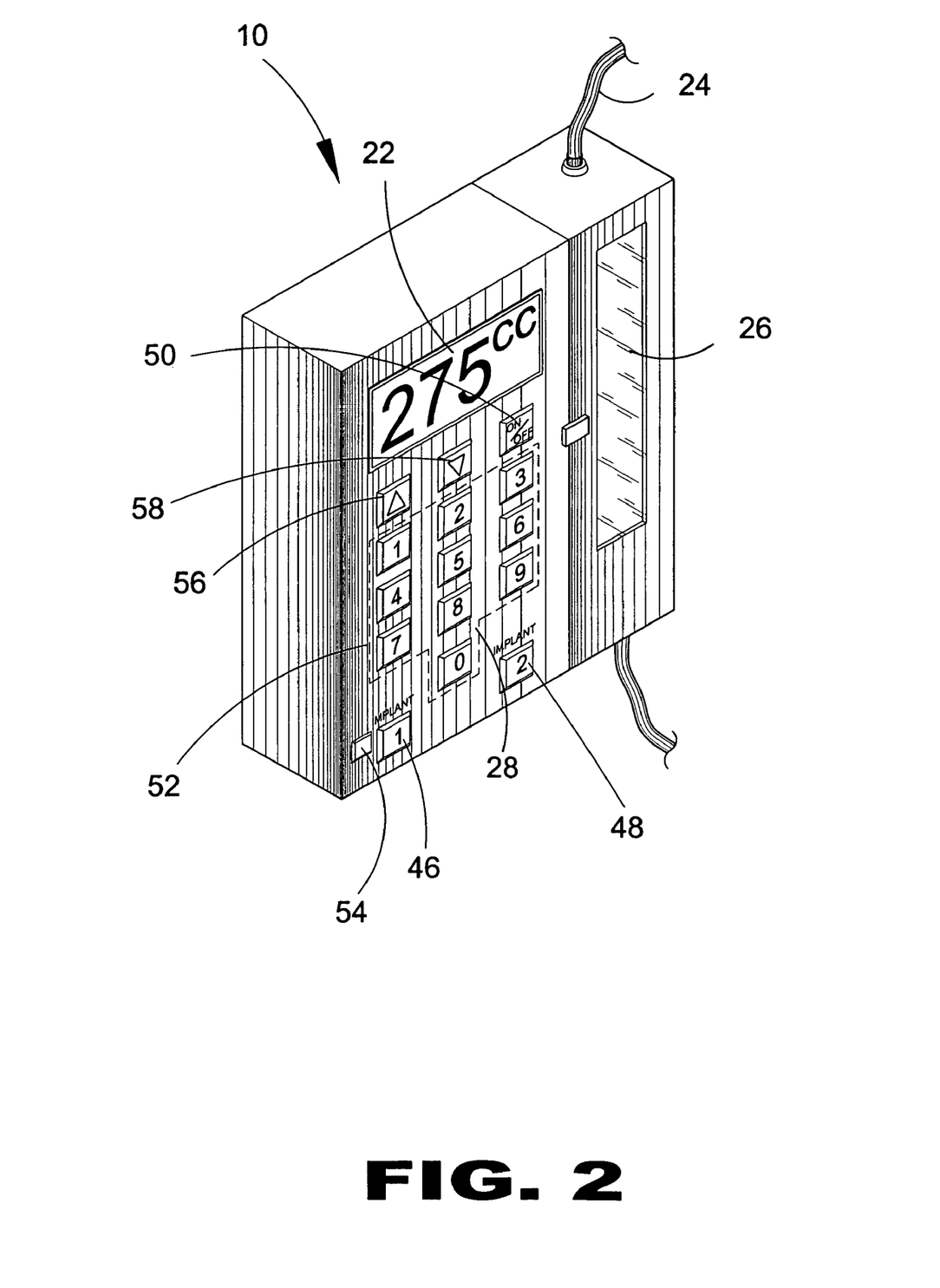
FIG. 2 is a perspective view of the implant fill device of the present invention.

FIG. 2 is a perspective view of the present invention. The present invention is a programmable pump for breast implant fill having means for specifying an amount of material to be dispensed, and an auxiliary means forming an integral part therewith for varying the quantity of material dispensed.

The implant fill pump system 10 of the present invention comprises a power source 14, a housing 44, and a three-way valve 20. The power source 14 is attached to the housing 44 and supplies the power to the implant fill pump system 10. Housing 44 includes a control pad 28, a set digital readout display 22, and a display 23 positioned on a side thereof. The housing 14 also includes a translucent intravenous (IV) fluid pump chamber 26 for retaining a fluid therein. A fluid source 16 is attached to housing 44 via a tube 24. A portion of the tube 24 is placed in the fluid pump chamber 26. The remainder of the tube 24 extends externally from the housing 44 and is connected to a three-way valve 20. An first implant tube 60 extends from the three-way valve 20 to an a first implant 30, which is located in one of two breasts 12. A second implant tube 62 extends from the three-way valve 20 to a second implant 31, which is located in one of two breasts 12 that does not contain the first implant 30.

The system 10 of the present invention allows for the implants 30,31 to be precisely filled in cubic centimeter (cc) volume of fluid. The user programs the desired CC's of fluid using the control pad 28 to be pumped by the system to fill at least one of the first implant 30 and second implant 31. The user selectively depresses the at least one of the first implant button 46 and the second implant button 48, to fill the appropriate implant.

The implant fill pump system 10 pumps the user-specified amount of an fluid 32 from the source 16 through the tube 24, which travels through the fluid pump chamber 26 and connects to a first port of the three-way valve 20 positioned external to housing 44. As the fluid 32 is pumped through the three-way valve 20, a monitoring mechanism 64 senses the amount of fluid 32 that has passed therethrough. The amount of fluid sensed is then displayed on the display 22. To add fluid 32 to an implant 30,31, a user increases the amount using the keypad 28 and the newly increased amount is shown on the display 22. The fluid pump chamber 26 contains a pumping mechanism 42 as shown in FIG. 7, including but not limited to a peristaltic or a cardiac pump, which pumps the user-specified amount of fluid 32 in the tube 24 through the three-way valve 20 and into one of first implant tube 60 and further to the first implant 30 or the second implant tube 62 and further to the second implant 31.

Figure 3:
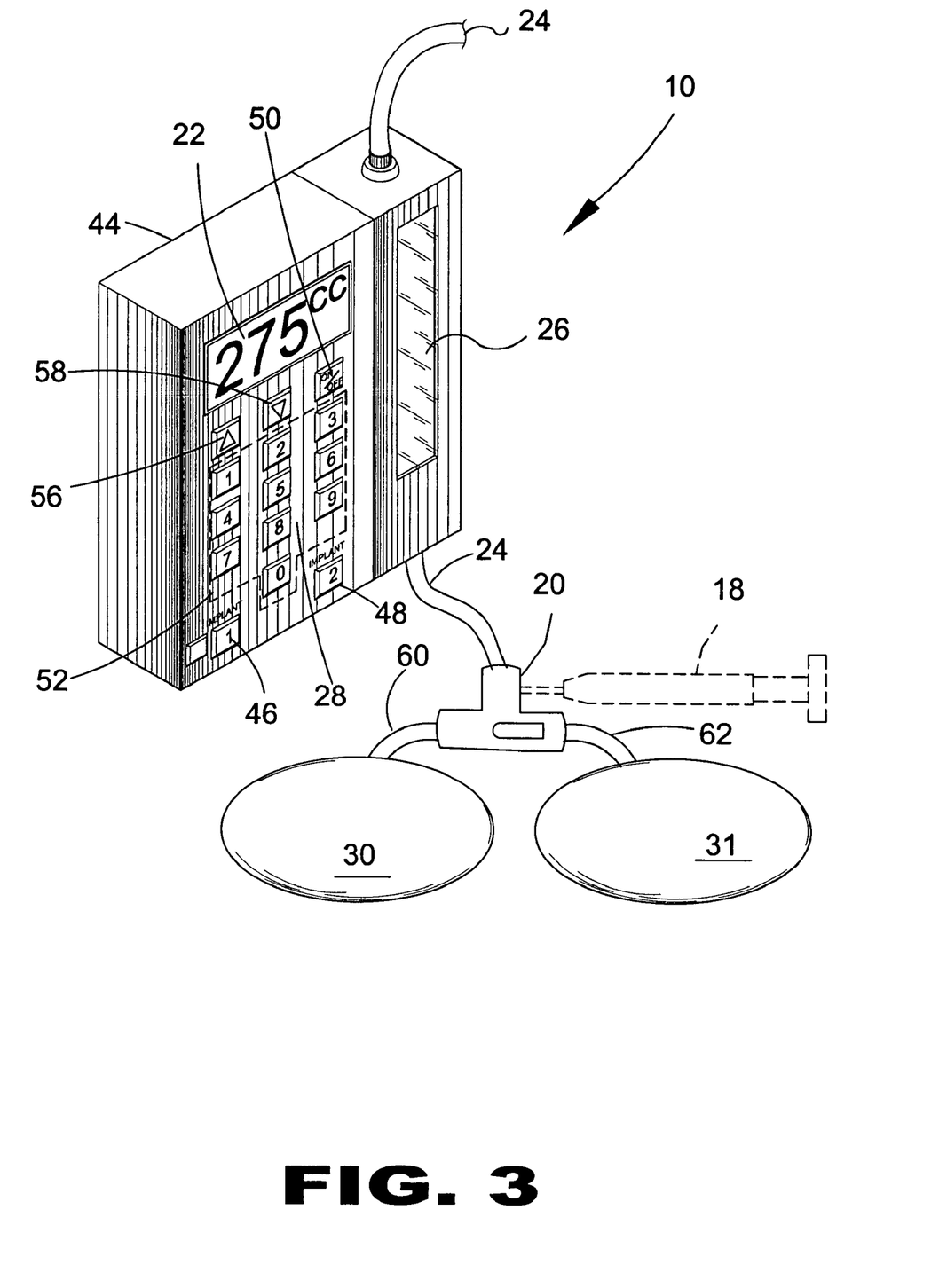
FIG. 3 is a perspective view of the implant fill device of the present invention.

As the fluid 32 is pumped through the three-way valve 20, shown in FIG. 3, a monitoring mechanism 64 senses how much fluid 32 has passed therethrough and the amount is displayed in the display 22. Should the user enter an undesired number, they could delete said undesired number by depressing a delete-button 54. The control pad 28 has an up-button 56 and a down-button 58 to increase or decrease the cubic centimeter (cc) volume in increments of one cc. The control pad 28 has a first implant button 46 and a second implant button 48, and upon depressing either button 46,48 the user selects the corresponding implant 30,31 to be filed by the pump system 10 of the present invention. The implant fill pump system 10 then pumps the user-specified amount of an fluid 32 from the fluid source 16, shown in FIG. 1, through the tube 24, which travels through the fluid pump chamber 26 and connects to the three-way valve 20, which is external to housing 44 as shown in FIGS. 1 and 3. To add fluid 32 to an implant 30 or 31, increase the number in the set digital readout display 22. The control pad 28 further includes numerical buttons 52 as well as an increase button 56 and a decrease button 58. The numerical buttons 52 and increase and decrease buttons 56 and 58, respectively, allow the user to adjust the amount of fluid 32 to be pumped by the system 10 of the present invention. The control pad 28 also contains a reverse pump button 68.

When a user determines the implant 30 or 31 contains too much fluid 32, a lower cc value than the originally input cc value is entered using any combination of buttons 52, 56 and 58. When a monitoring mechanism 64 in the three-way valve 20 senses an amount of fluid 32 greater than the set amount, an audio alert 66 will be activated. The user can selectively depress the reverse pump button 68 which will remove fluid 32 from the implant 30 or 31 until the amount of fluid 32 remaining in the implant 30 or 31 is equal to the re-set volume amount. The removed IV fluid 32 is deposited in a fluid vent 38, shown in FIG. 6.

FIG. 3 is a perspective view of the implant fill pump system 10 of the present invention. The implant fill pump system 10 of the present invention comprises a power source 14, a housing 44, and a three-way valve 20. The power source 14 is attached to the housing 44 and supplies the power to the implant fill pump system 10. Housing 44 includes a control pad 28, a set digital readout display 22, and a display 23 positioned on a side thereof. The housing 14 also includes a translucent intravenous (IV) fluid pump chamber 26 for retaining a fluid therein. A fluid source 16 is attached to housing 44 via a tube 24. A portion of the tube 24 is placed in the fluid pump chamber 26. The remainder of the tube 24 extends externally from the housing 44 and is connected to a three-way valve 20. An first implant tube 60 extends from the three-way valve 20 to an a first implant 30, which is located in one of two breasts 12. A second implant tube 62 extends from the three-way valve 20 to a second implant 31, which is located in one of two breasts 12 that does not contain the first implant 30.

The system 10 of the present invention allows for the implants 30,31 to be precisely filled in cubic centimeter (cc) volume of fluid. The user programs the desired CC's of fluid using the control pad 28 to be pumped by the system to fill at least one of the first implant 30 and second implant 31. The user selectively depresses the at least one of the first implant button 46 and the second implant button 48, to fill the appropriate implant.

The implant fill pump system 10 pumps the user-specified amount of an fluid 32 from the source 16 through the tube 24, which travels through the fluid pump chamber 26 and connects to a first port of the three-way valve 20 positioned external to housing 44. As the fluid 32 is pumped through the three-way valve 20, a monitoring mechanism 64 senses the amount of fluid 32 that has passed therethrough. The amount of fluid sensed is then displayed on the display 22. To add fluid 32 to an implant 30,31, a user increases the amount using the keypad 28 and the newly increased amount is shown on the display 22. The fluid pump chamber 26 contains a pumping mechanism 42 as shown in FIG. 7, including but not limited to a peristaltic or a cardiac pump, which pumps the user-specified amount of fluid 32 in the tube 24 through the three-way valve 20 and into one of first implant tube 60 and further to the first implant 30 or the second implant tube 62 and further to the second implant 31.

As the fluid 32 is pumped through the three-way valve 20, shown in FIG. 3, a monitoring mechanism 64 senses how much fluid 32 has passed therethrough and the amount is displayed in the display 22. Should the user enter an undesired number, they could delete said undesired number by depressing a delete-button 54. The control pad 28 has an up-button 56 and a down-button 58 to increase or decrease the cubic centimeter (cc) volume in increments of one cc. The control pad 28 has a first implant button 46 and a second implant button 48, and upon depressing either button 46,48 the user selects the corresponding implant 30,31 to be filed by the pump system 10 of the present invention. The implant fill pump system 10 then pumps the user-specified amount of an fluid 32 from the fluid source 16, shown in FIG. 1, through the tube 24, which travels through the fluid pump chamber 26 and connects to the three-way valve 20, which is external to housing 44 as shown in FIGS. 1 and 3. To add fluid 32 to an implant 30 or 31, increase the number in the set digital readout display 22. The control pad 28 further includes numerical buttons 52 as well as an increase button 56 and a decrease button 58. The numerical buttons 52 and increase and decrease buttons 56 and 58, respectively, allow the user to adjust the amount of fluid 32 to be pumped by the system 10 of the present invention. The control pad 28 also contains a reverse pump button 68.

When a user determines the implant 30 or 31 contains too much fluid 32, a lower cc value than the originally input cc value is entered using any combination of buttons 52, 56 and 58. When a monitoring mechanism 64 in the three-way valve 20 senses an amount of fluid 32 greater than the set amount, an audio alert 66 will be activated. The user can selectively depress the reverse pump button 68 which will remove fluid 32 from the implant 30 or 31 until the amount of fluid 32 remaining in the implant 30 or 31 is equal to the re-set volume amount. The removed IV fluid 32 is deposited in a fluid vent 38, shown in FIG. 6.

To manually make fine adjustments to the quantity of fluid 32 contained in either the first implant 30 or second implant 31, the three-way valve 20 permits the user to attach a syringe 18 a port of three-way valve 20. Upon connecting the syringe 18, the physician is able to move the plunger to finely adjust the amount of fluid 32 contained therein.

Figure 4:
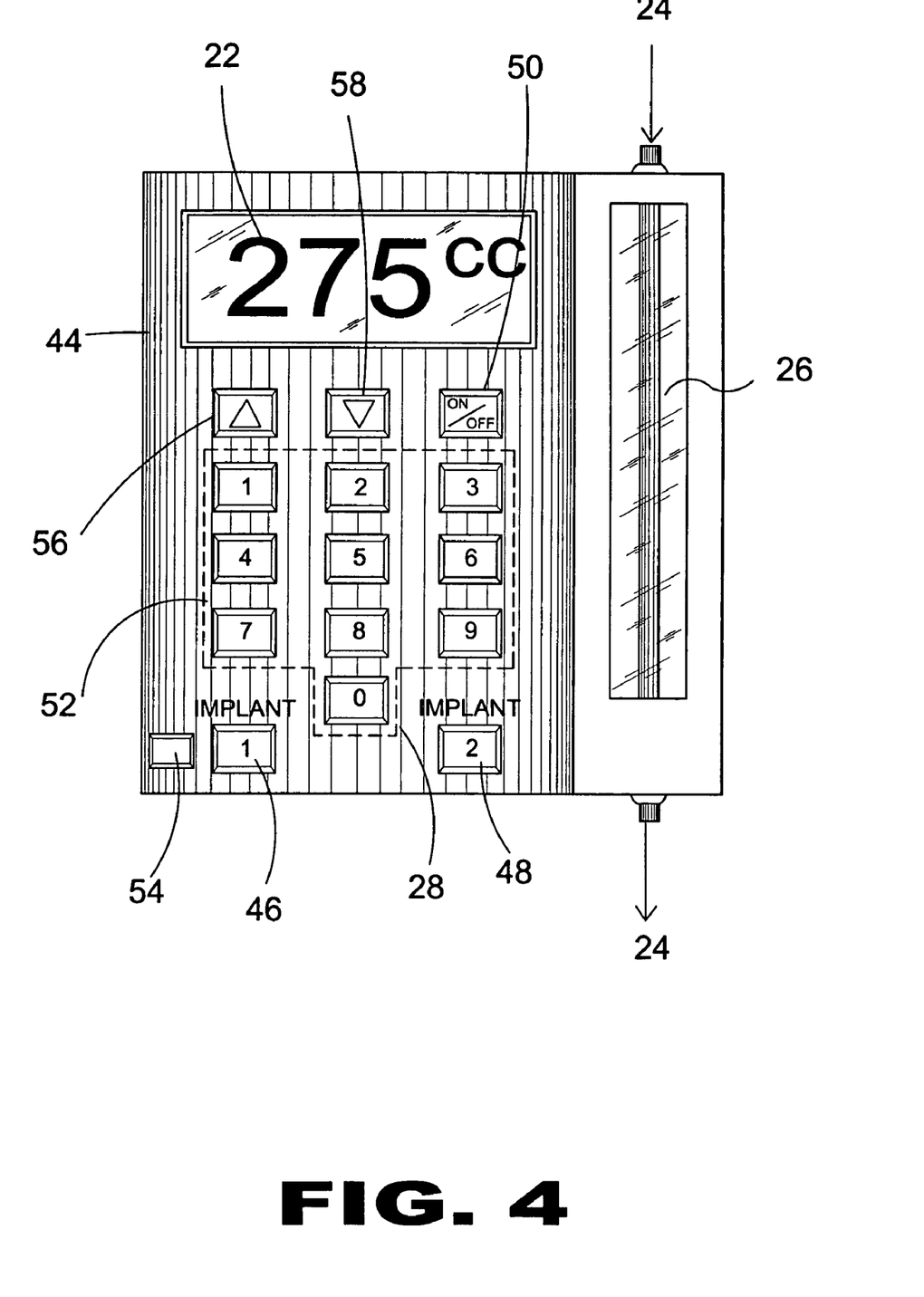
FIG. 4 is a front view of the implant fill device of the present invention.

FIG. 4 is a front view of the implant fill pump system 10 of the present invention. The implant fill pump system 10 of the present invention comprises a power source 14, a housing 44, and a three-way valve 20. The power source 14 is attached to the housing 44 and supplies the power to the implant fill pump system 10. Housing 44 includes a control pad 28, a set digital readout display 22, and a display 23 positioned on a side thereof. The housing 14 also includes a translucent intravenous (IV) fluid pump chamber 26 for retaining a fluid therein. A fluid source 16 is attached to housing 44 via a tube 24. A portion of the tube 24 is placed in the fluid pump chamber 26. The remainder of the tube 24 extends externally from the housing 44 and is connected to a three-way valve 20. An first implant tube 60 extends from the three-way valve 20 to an a first implant 30, which is located in one of two breasts 12. A second implant tube 62 extends from the three-way valve 20 to a second implant 31, which is located in one of two breasts 12 that does not contain the first implant 30.

The system 10 of the present invention allows for the implants 30,31 to be precisely filled in cubic centimeter (cc) volume of fluid. The user programs the desired CC's of fluid using the control pad 28 to be pumped by the system to fill at least one of the first implant 30 and second implant 31. The user selectively depresses the at least one of the first implant button 46 and the second implant button 48, to fill the appropriate implant.

The implant fill pump system 10 pumps the user-specified amount of an fluid 32 from the source 16 through the tube 24, which travels through the fluid pump chamber 26 and connects to a first port of the three-way valve 20 positioned external to housing 44. As the fluid 32 is pumped through the three-way valve 20, a monitoring mechanism 64 senses the amount of fluid 32 that has passed therethrough. The amount of fluid sensed is then displayed on the display 22. To add fluid 32 to an implant 30,31, a user increases the amount using the keypad 28 and the newly increased amount is shown on the display 22. The fluid pump chamber 26 contains a pumping mechanism 42 as shown in FIG. 7, including but not limited to a peristaltic or a cardiac pump, which pumps the user-specified amount of fluid 32 in the tube 24 through the three-way valve 20 and into one of first implant tube 60 and further to the first implant 30 or the second implant tube tube 62 and further to the second implant 31.

As the fluid 32 is pumped through the three-way valve 20, shown in FIG. 3, a monitoring mechanism 64 senses how much fluid 32 has passed therethrough and the amount is displayed in the display 22. Should the user enter an undesired number, they could delete said undesired number by depressing a delete-button 54. The control pad 28 has an up-button 56 and a down-button 58 to increase or decrease the cubic centimeter (cc) volume in increments of one cc. The control pad 28 has a first implant button 46 and a second implant button 48, and upon depressing either button 46,48 the user selects the corresponding implant 30,31 to be filed by the pump system 10 of the present invention. The implant fill pump system 10 then pumps the user-specified amount of an fluid 32 from the fluid source 16, shown in FIG. 1, through the tube 24, which travels through the fluid pump chamber 26 and connects to the three-way valve 20, which is external to housing 44 as shown in FIGS. 1 and 3. To add fluid 32 to an implant 30 or 31, increase the number in the set digital readout display 22. The control pad 28 further includes numerical buttons 52 as well as an increase button 56 and a decrease button 58. The numerical buttons 52 and increase and decrease buttons 56 and 58, respectively, allow the user to adjust the amount of fluid 32 to be pumped by the system 10 of the present invention. The control pad 28 also contains a reverse pump button 68.

When a user determines the implant 30 or 31 contains too much fluid 32, a lower cc value than the originally input cc value is entered using any combination of buttons 52, 56 and 58. When a monitoring mechanism 64 in the three-way valve 20 senses an amount of fluid 32 greater than the set amount, an audio alert 66 will be activated. The user can selectively depress the reverse pump button 68 which will remove fluid 32 from the implant 30 or 31 until the amount of fluid 32 remaining in the implant 30 or 31 is equal to the re-set volume amount. The removed IV fluid 32 is deposited in a fluid vent 38, shown in FIG. 6.

Figure 5:
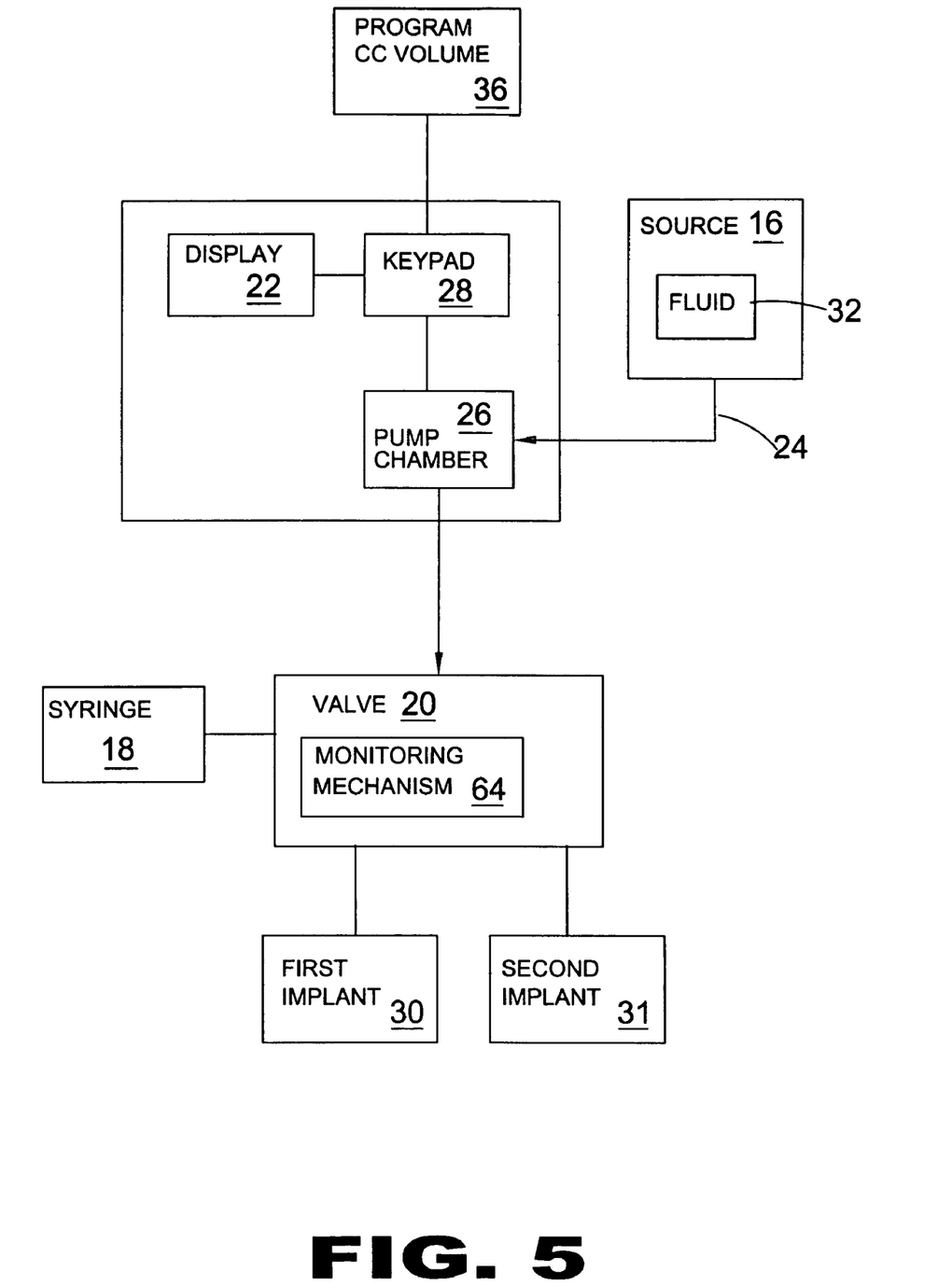
FIG. 5 is a block diagram of the implant fill device of the present invention.

FIG. 5 is a block diagram of the implant fill pump system 10 of the present invention. The pump system 10 of the present invention includes a programmed amount of fluid 36 to be pumped thereby. This is entered into the system as described hereinabove with specific reference to FIGS. 2-4 using the keypad 28. The system 10 further includes the fluid pump chamber 26 and display 22 for displaying the value 36 entered by the user. Positioned externally and connected to the housing 18 is the three-way value 20 which is connected to the syringe 18 and each of the first implant 30 and the second implant 31. The three-way valve 20 has a monitoring mechanism 64 to indicate the number of cc's presently in at least one of the first implant 30 and second implant 31.

The operation of the implant fill pump system 10 of the present invention will now be described with reference to the above figure. The user programs the cc volume of fluids to be pumped 36 into the implant fill pump system 10 via the control pad 28, shown in FIG. 1. The user specified amount of fluid 32 is displayed by the display 22. Fluid 32 enters the fluid pump chamber 26 in the housing 18 from the fluid source 16. The fluid pump chamber 26 contains a pumping mechanism, including but not limited to a peristaltic or a cardiac pump, which pumps the user-specified amount of fluid 32 in the tube 24 through the three-way valve 20 and into one of the first implant tube 60 or the second implant tube 62, which attaches to the corresponding first implant 30 and the second implant 31 respectively. The monitoring mechanism 64 monitors the amount of fluid 32 in each of the implants 30,31 and these values may be selectively displayed on the display 22. To manually make fine adjustments to the volume of fluid 32 in the implants 30,31, fluid 32 can be at least one of added and removed via the syringe 18 which is also connected to the valve 20.

Figure 6:
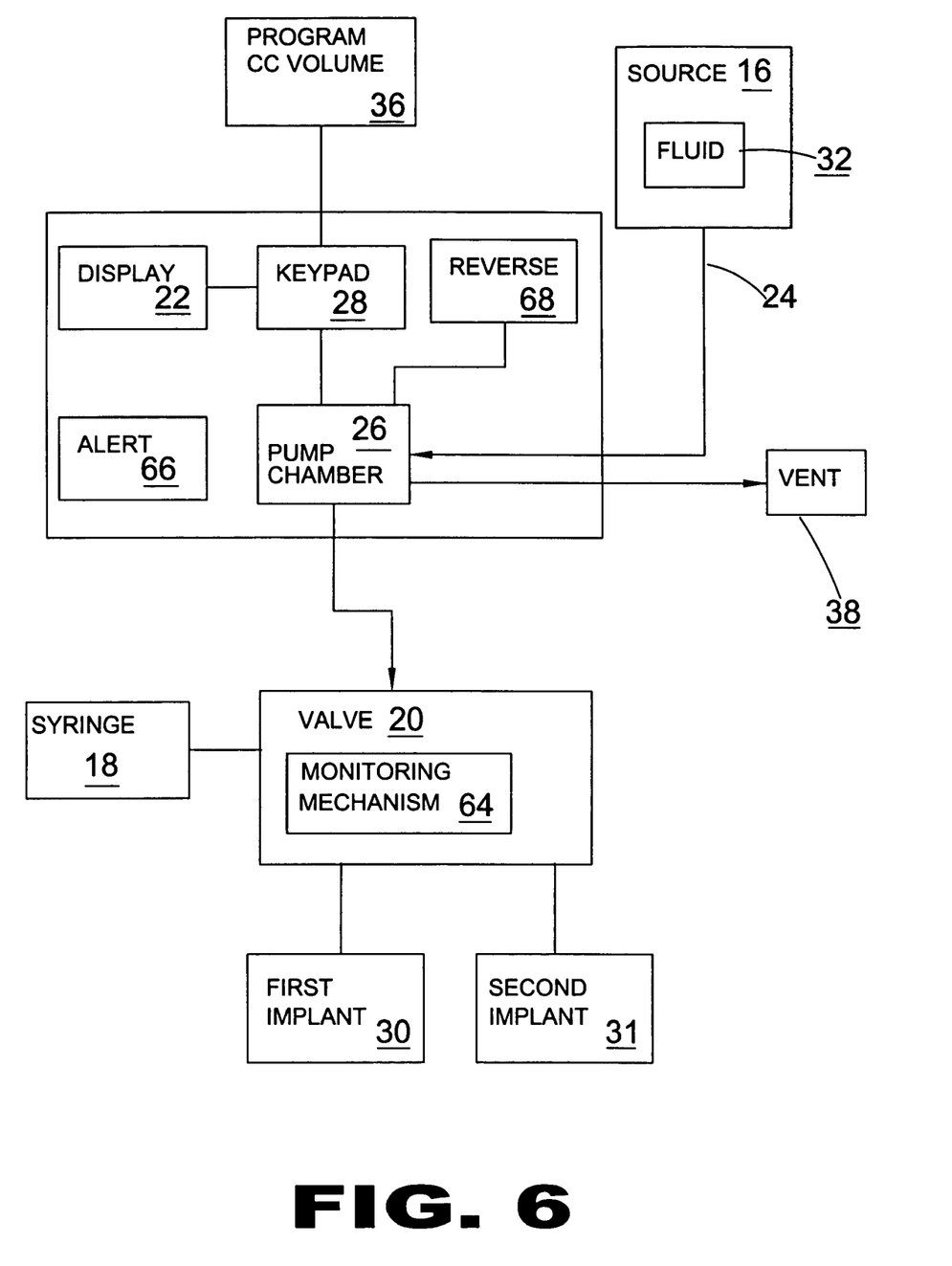
FIG. 6 is a block diagram of the implant fill device of the present invention.

FIG. 6 is a block diagram of the present invention with a vent means. The pump system 10 of the present invention includes a programmed amount of fluid 36 to be pumped thereby. This is entered into the system as described hereinabove with specific reference to FIGS. 2-4 using the keypad 28. The system 10 further includes the fluid pump chamber 26 and display 22 for displaying the value 36 entered by the user. Positioned externally and connected to the housing 18 is the three-way value 20 which is connected to the syringe 18 and each of the first implant 30 and the second implant 31. The three-way valve 20 has a monitoring mechanism 64 to indicate the number of cc's presently in at least one of the first implant 30 and second implant 31. The system 10 may also include a fluid vent 38 connected to the pump chamber 26.

The operation of the implant fill pump system 10 of the present invention will now be described with reference to the above figure. The user programs the cc volume of fluids to be pumped 36 into the implant fill pump system 10 via the control pad 28, shown in FIG. 1. The user specified amount of fluid 32 is displayed by the display 22. Fluid 32 enters the fluid pump chamber 26 in the housing 18 from the fluid source 16. The fluid pump chamber 26 contains a pumping mechanism, including but not limited to a peristaltic or a cardiac pump, which pumps the user-specified amount of fluid 32 in the tube 24 through the three-way valve 20 and into one of the first implant tube 60 or the second implant tube 62, which attaches to the corresponding first implant 30 and the second implant 31 respectively. The monitoring mechanism 64 monitors the amount of fluid 32 in each of the implants 30,31 and these values may be selectively displayed on the display 22. To manually make fine adjustments to the volume of fluid 32 in the implants 30,31, fluid 32 can be at least one of added and removed via the syringe 18 which is also connected to the valve 20.

Alternatively, the pumping mechanism of fluid pump chamber 26 is a reversible pump with the ability to remove fluid 32 from an implant 30 or 31. To manually make adjustments to implant 30 or 31, fluid 32 can be removed by re-setting the cc volume of fluids to be pumped using the keypad 28. When the monitoring mechanism 64 in the three-way valve 20 senses an amount of fluid 32 greater than the set amount, the audio alert 66 will be activated. The user will now depress the reverse pump button 68 which will remove fluid 32 from the implant 30 or 31 until the amount of fluid 32 remaining in the implant 30 or 31 is equal to the re-set volume amount. The removed fluid 32 is deposited in a fluid vent 38. Alternatively, fluid 32 can be manually removed via a syringe 18 which is attached at the base of the three-way valve 20 where the IV tube 24 is connected.

FIG. 7 is an illustrative view of the peristaltic pump of the present invention. The present figure shows the pumping mechanism 42 of the implant fill pump system 10 to be a peristaltic pump. The pump 42 is contained within the housing 18 and extends partially into the pump chamber 26. The pump 42 is substantially circular in shape and includes a plurality of rollers 43 positioned around a periphery thereof. The IV fluid pump chamber 26 contains a tubing retainer 40 having at least one roller 434 positioned thereon. The tubing retainer 40 prevents the horizontal movement of the IV tube 24 when pressure from the peristaltic pump is applied to the tube 24. The pump 42 rotates about a center point 41 in a direction of the arrow labeled with reference numeral 45. As the arms of the peristaltic pump 42 rotate, the rollers 43 on the rotating arms and the rollers on the tubing retainer 40 pinch the tube 24 causing the fluid 32 to move therealong. Alternatively the pump can rotate bi-directionally thereby allowing the pump 42 to move the fluid in two directions along the length of the tube 24.

While this invention is described for the purpose of filling a breast implant, the pumping system 10 of the present invention may be used to fill any fluid-filled implant that may be inserted into the human body. Furthermore, it should noted that preferably the fluid 32 is saline. However, the fluid 32 may be any fluid medically accepted and approved by the Food and Drug Administration for use in filling an implanted object in a human body.

It will be understood that each of the elements described above, or two or more together may also find a useful application in other types of methods differing from the type described above.

Preferably, the truss members 11 and the sleeves 16 are formed from steel thereby providing greater support to the resulting building structure as well as allowing the resulting building structure to be formed in segments and combined and connected to one another to form the resulting building. However, the truss system 10 may be formed using any material that is strong and lightweight that is also easily maneuverable.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A system for pumping a fluid into a body implant comprising:
   a) a housing having a pump chamber containing a pump for pumping said fluid;
   b) a source of fluid connected to said pump;
   c) a valve connected between said pump and said implant through which said fluid flows;

d) said housing having a digital readout display and a keypad for selecting and displaying a volume of fluid to be delivered by said pump though said valve to said implant;
e) said valve containing a monitoring mechanism for sensing the amount of fluid flowing through said valve, said display showing said amount of fluid;
f) wherein said source, said pump and said valve are connected via a tube;
g) wherein said pump is selected from the group consisting of a peristaltic pump and a cardiac pump;
h) wherein said keypad comprises a numerical keypad and a plurality of directional buttons for entering and changing the selected volume;
i) said valve has a port for receiving a syringe for adding or removing fluid from said implant; and
j) wherein said pump is a bi-directional pump.

2. The system as recited in claim 1, wherein said peristaltic pump comprises a circular center member having a plurality of arms extending peripherally therearound, each of said plurality of arms includes at least one roller positioned thereon and further comprising a tube retainer have at least one roller positioned thereon, wherein said plurality of arms rotates about said center member and said rollers pinch said tube therebetween and cause said fluid to be moved along a length thereof.

3. The system as recited in claim 1, wherein said monitoring mechanism, upon determining that an amount of said fluid received by said implant is greater than said selected volume, causes said pump to operate in an opposite direction thereby removing an amount of said fluid equal to the difference between a received amount and said selected volume desired amount.

4. The system as recited in claim 3, further comprising an alert mechanism for at least one of audibly and visually alerting a user that said received amount of fluid is greater than said selected volume of fluid.

5. The system as recited in claim 4, wherein said implant is at least one of a breast implant, pectoral implant and a calf implant.

6. A system for pumping a fluid into a pair of breast implants comprising:
a) a housing having a pump chamber containing a pump for pumping said fluid;
b) a source of fluid connected to said pump;
c) a three-way valve having an inlet connected to said pump and a pair of outlets connected to each of said implants, respectively;
d) said housing have a digital readout display and a keypad for selecting and displaying a volume of fluid to be delivered by said pump through said valve to each of said implants;
e) said valve containing a monitoring mechanism for sensing the amounts of fluid flowing through said valve to each of said implants, said display showing said amounts of fluid;
f) the inlet to said valve having a port to receive a syringe for adding and removing fluid from said implants; and
g) said keypad comprising a numerical keypad, a plurality of directional buttons for entering and changing selected volumes, a reverse button for withdrawing fluid from an implant, and first and second buttons for selecting the implant for delivery of fluid.

7. The system as recited in claim 6, having a vent in said pump chamber for discharging fluid.

\* \* \* \* \*